United States Patent
Royer et al.

(10) Patent No.: US 10,006,853 B2
(45) Date of Patent: Jun. 26, 2018

(54) VIAL AND CAP FOR TURBIDITY STANDARD

(71) Applicant: Hach Company, Loveland, CO (US)

(72) Inventors: Douglas Ford Royer, Gilbert, IA (US); Charles C. Johnson, Loveland, CO (US); Andreas Golitz, Moers (DE); Bas de Heij, Dormagen (DE)

(73) Assignee: HACH COMPANY, Loveland, CO (US)

( * ) Notice: Subject to any disclaimer, the term of this patent is extended or adjusted under 35 U.S.C. 154(b) by 0 days. days.

(21) Appl. No.: 15/486,125

(22) Filed: Apr. 12, 2017

(65) Prior Publication Data

US 2018/0113067 A1     Apr. 26, 2018

Related U.S. Application Data

(60) Provisional application No. 62/412,726, filed on Oct. 25, 2016.

(51) Int. Cl.
   *G01N 21/03*     (2006.01)
   *G01N 21/51*     (2006.01)

(52) U.S. Cl.
   CPC ......... *G01N 21/0303* (2013.01); *G01N 21/51* (2013.01); *G01N 2201/068* (2013.01)

(58) Field of Classification Search
   CPC ............... G01N 21/0303; G01N 21/51; G01N 2201/068

USPC .............................................. 356/243.1, 246
See application file for complete search history.

(56) References Cited

U.S. PATENT DOCUMENTS

| | | | | |
|---|---|---|---|---|
| 3,923,158 A | * | 12/1975 | Fornaa | B07C 5/126 209/526 |
| 3,963,918 A | * | 6/1976 | Jensen | B07C 5/3412 250/216 |
| 4,121,103 A | * | 10/1978 | Calhoun | G01F 23/2921 250/339.05 |
| 2005/0110989 A1 | * | 5/2005 | Schermer | G01N 21/253 356/246 |

* cited by examiner

*Primary Examiner* — Roy M Punnoose
(74) *Attorney, Agent, or Firm* — Ference & Associates LLC

(57) ABSTRACT

An embodiment provides a turbidimeter standard ampule, including: a main part composed of glass and containing therein a formazin solution comprising a formazine polymer diluted in a solvent; the main part including a lens positioned in a bottom edge thereof and permitting entry of light from a turbidimeter; the main part having glass sides and permitting redirected light to exit the glass sides for detection by a photodetector of the turbidimeter; an upper part composed of glass and being attached to the main part; and an opaque cap on the upper part, the opaque cap blocking light from entering the upper part of the ampule. Other embodiments are described and claimed.

17 Claims, 7 Drawing Sheets

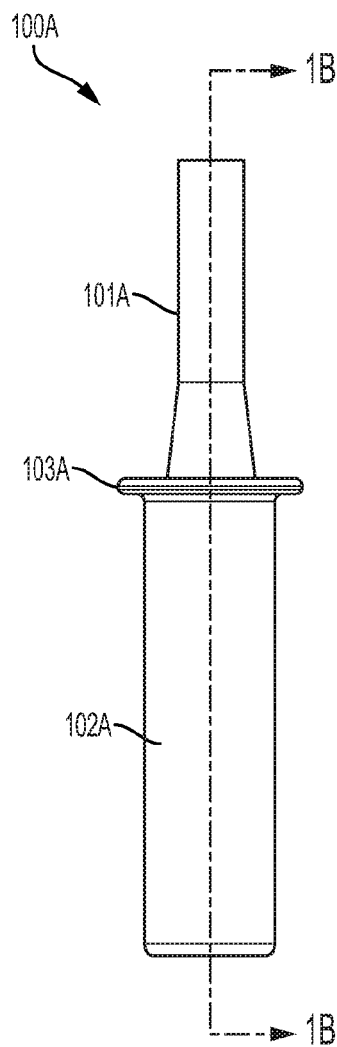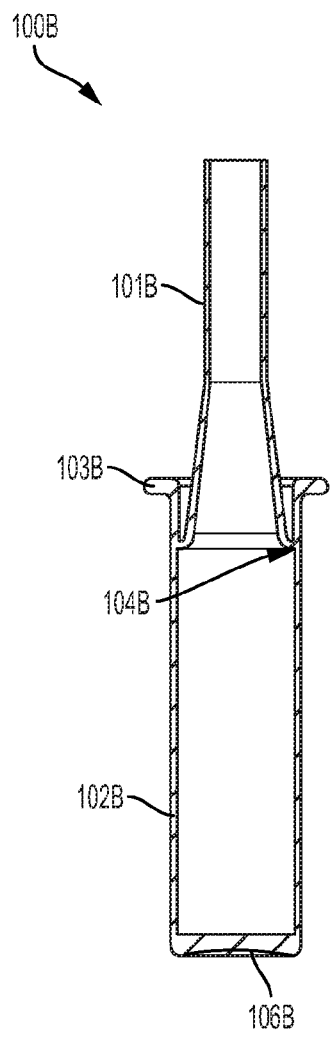
FIG. 1A
FIG. 1B

VIAL AND CAP FOR TURBIDITY STANDARD

CROSS REFERENCE TO RELATED APPLICATIONS

This application claims priority to Provisional Patent Application Ser. No. 62/412,726, filed on 25 Oct. 2016, and entitled VIAL AND CAP FOR TURBIDITY STANDARD, the content of which is incorporated by reference herein.

FIELD

The subject matter described herein is in the general field of water quality measurement, specifically for vials and caps for turbidity standards.

BACKGROUND

Turbidimeters measure the turbidity (cloudiness, haziness) of a solution, e.g., water, by viewing light that passes through the solution and determining how much light is transmitted or reflected (depending on the detection technique of the turbidimeter). For example, the Hach Company TU5 Series turbidimeters measure turbidity by directing a laser into a sample to scatter off suspended particles in solution. The light that is scattered at a 90° angle from the incident beam is reflected through a conical mirror in a 360° ring around the sample before it is captured by a detector.

The amount of light scattered is proportional to the turbidity of the sample. If the turbidity of the sample is negligible, little light will be scattered and detected by the photocell, and the turbidity reading will be low. High turbidity, on the other hand, will cause a high level of light scattering and result in a high reading.

Turbidimeters need to be calibrated. This is accomplished using a standard solution of known turbidity. For example, a standard containing the formazine (formazin) polymer is commonly used. The formazine polymer is dissolved into solution to form a standard solution of known turbidity unit values (i.e., having a known amount of nephelometric turbidity units (NTUs)), creating a formazin stock solution. For example, 5 g/L hydrazine sulfate is mixed with 50 g/L hexamethylenetetramine in ultrapure water, and developed over 24 hours at 25° C. to produce a suspension with 4000NTU (formazin stock solution). This formazin stock solution may then be diluted to an appropriate value to act as a standard for a given detection range. Information on standard units and solutions commonly used in this area is found in the international standard (ISO 7027).

BRIEF SUMMARY

In summary, one embodiment provides a turbidimeter standard ampule, comprising: a main part comprising glass and containing therein a formazin solution comprising a formazine polymer diluted in a solvent; the main part comprising a lens positioned in a bottom edge thereof and permitting entry of light from a turbidimeter; the main part having glass sides and permitting redirected light to exit the glass sides for detection by a photodetector of the turbidimeter; an upper part comprising glass and being attached to the main part; and an opaque cap on the upper part, the opaque cap blocking light from entering the upper part of the ampule.

Another embodiment provides a kit, comprising: a plurality of turbidimeter standard ampules, each of the plurality of turbidity standard ampules comprising: a main part comprising glass and containing therein a formzain solution comprising a formazine polymer diluted in a solvent; the main part comprising a lens positioned in a bottom edge thereof and permitting entry of light from a turbidimeter; the main part having glass sides and permitting redirected light to exit the glass sides for detection by a photodetector of the turbidimeter; an upper part comprising glass and being attached to the main part; and an opaque cap that fits over the upper part, the opaque cap blocking light from entering the upper part of the ampule; wherein the plurality of turbidity standard ampules comprise a range of different formazine standard solutions.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

BRIEF DESCRIPTION OF THE DRAWINGS

FIG. 1(A-B) illustrates an example ampule or vial and cross section thereof for a turbidity standard according to a first embodiment.

DETAILED DESCRIPTION

Figure 2:
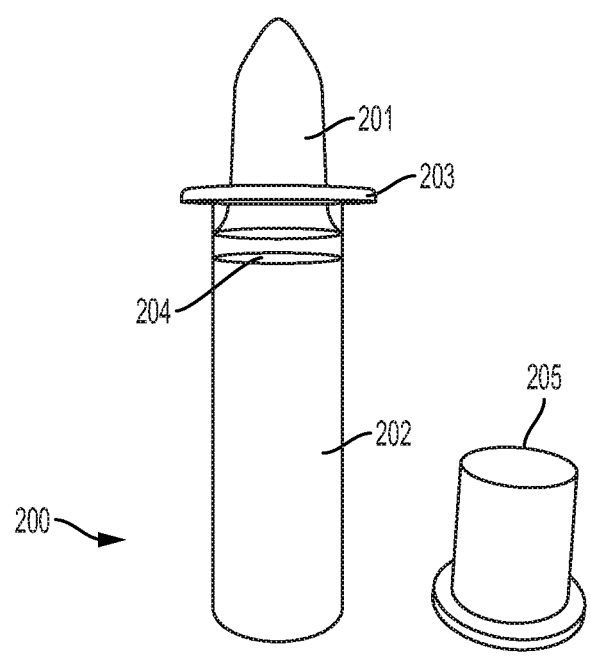
FIG. 2 illustrates an example ampule or vial and cap for a turbidity standard according to a second embodiment.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of example embodiments. One skilled in the relevant art will recognize, however, that various embodiments can be practiced without one or more of the specific details, or with other methods, components, materials, et cetera. In other instances, well-known structures, materials, or operations are not shown or described in detail. The following description is intended only by way of example, and simply illustrates certain example embodiments.

The formazin stock solution is not shelf stable. The formazine polymer has shown instability when in contact with certain plastics even when dissolved in a solvent such as ultrapure water. This is true even for a "stabilized" version of the formazine standard, for example, formazine polymer diluted in a stabilizing solvent such as StablCal® standard available from Hach Company of Loveland Colo., USA. Mitigation techniques for addressing this issue have included application of a low density polyethylene (LDPE) liner in the standard or vial. However, the LDPE liner can react with the formazine polymer and cause instability.

Accordingly, an embodiment provides a glass ampule or vial (the terms ampule and vial are used interchangeably herein) that contains a stabilized formazin standard (e.g., Hach StablCal® standard) and precludes the need to utilize a liner to avoid an unstable standard solution. The glass ampule or vial prevents possible formazine polymer interaction or chemical reaction with a plastic cap or plastic sleeve of a vial, thus increasing the accuracy of turbidity measurement. An embodiment provides the ampule does not include plastic in contact with the formazin solution.

An embodiment provides a glass ampule in two parts, i.e., a main part and an upper part, which may be fused or sealed together via heat treatment. For example, in an embodiment, a glass upper part and glass lower part are flamed briefly to fuse the glass parts together. The flame sealing encapsulates the formazin standard within the glass ampule. This encapsulation within the glass ampule prevents possible formazine polymer interaction or chemical reaction with a plastic cap or plastic sleeve of a vial due the formazine polymer being reactive and adhering to the plastic which accelerates the degradation of the formazin standard resulting in inaccurate turbidity measurements.

In an embodiment, a cap is provided, e.g., a black or opaque cap, to the top (upper) part of the vial. The cap blocks light entry and exit from the top or upper part of the vial during use, e.g., insertion into a vial chamber. Additionally, the cap prevents the incident laser beam from re-entering the sample compartment of the turbidimeter or lower part of the vial. As used herein, a cap may be understood to include a covering or a coating applied to the upper part of the ampule, as well as a separate cap piece, e.g., formed as an opaque (e.g., black) plastic material that fits onto the upper part of the ampule.

A further embodiment provides a method of using an ampule(s) or a vial(s) for lengthening the time over which accurate standardization or calibration of a turbidimeter can occur. The ampule(s) or vial(s) contain known concentrations of the formazine polymer solution which can be used to calibrate the turbidimeter prior to measurement of an unknown sample in a more accurate manner.

Referring now to FIG. 1A, a plan view of a glass ampule 100A is illustrated. In FIG. 1(A-B) the glass ampule 100A/100B is about 108 mm in length, which is one non-limiting example.

As illustrated, the ampule 100A includes two parts, i.e., an upper part 101A, which in the example of FIG. 1 is about 43 mm in length and 11.6 mm in width at its lower margin, and a lower or main part 102A, about 65 mm in length. The lower or main part 102A houses the formazin standard therein and is inserted into a vial chamber or compartment of a turbidimeter (refer to FIG. 6).

The lower 102A and upper 101A parts are fused together by heat treatment at joint portion 103A, which also forms a lip for seating the ampule 100A in a vial compartment of a turbidimeter. The upper part 103A is inserted into a cavity of the main part 102A, and thereafter the upper part 103A and main part 102A are fused together. The flame sealing encapsulates the formazin standard within the glass ampule. This encapsulation within the glass ampule prevents possible formizine polymer interaction or chemical reaction with a plastic cap or plastic sleeve of the vial due the formizine polymer being reactive and adhering to the plastic which accelerates the degradation of the formizin standard resulting in inaccurate turbidity.

The upper 101A and lower 102A parts may be formed of a glass, such as borosilicate glass, or the like. For example, the lower part 102A, particularly a lens (106B) may be a borosilicate glass having a tradename of Borafloat 33. The rest of the ampule 100A body may be made from glass with a trade name of Duran TLB. The lens 106B may be formed of borosilicate glass or another type of glass having a higher purity for optical properties to allow adequate light entrance into the ampule for turbidity measurement. The lens may be flat or other shape allowing light to enter and exit the ampule on the glass sides and bottom. The preferred embodiment utilizes glass material such as borosilicate glass, or the like, in which the glass contains beneficial structural, thermal, chemical stability, and other beneficial optical properties.

FIG. 1B illustrates the ampule 100B in cross section. The upper 101B and lower 102B parts are joined together, for example by applying a flame to join portion 103B (or slightly below) to heat and fuse the glass of the upper 101B and lower 102B parts to one another, sealing the formazin standard therein. As shown in FIG. 1B, the flame treatment forms a fused part 104B.

Figure 3:
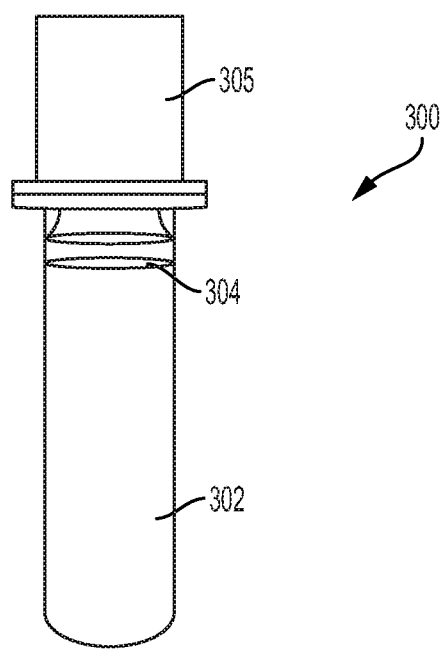
FIG. 3 illustrates an example ampule or vial and cap for a turbidity standard according to a second embodiment.

FIG. 2 illustrates an ampule 200 having the upper part 201 fused to the lower part 202, with the formazin standard contained therein. As illustrated in FIG. 2, a cap 205 that is not transparent is provided and fits over the upper part 201, e.g., is seated on top of the join portion/lip 203, in a circumferential manner. The cap 205, as illustrated in FIG. 3, is fitted onto the upper part 201. The cap 205 may be reversibly attached to the upper part 201 or may be fixed thereto. Again, a non-transparent or opaque coating or covering material applied to or integrated with the upper part 201 may be used as an equivalent to a cap. The fused part 204 is visible in FIG. 2.

FIG. 3 illustrates an ampule 300 where the cap 305 has been placed on the upper part (not visible in FIG. 3). The lower part 302 remains unobscured (for light entry and exit when inserted into a turbidimeter, as further explained in connection with FIGS. 5-7). The fused part 304 is again visible in FIG. 3.

Figure 4:
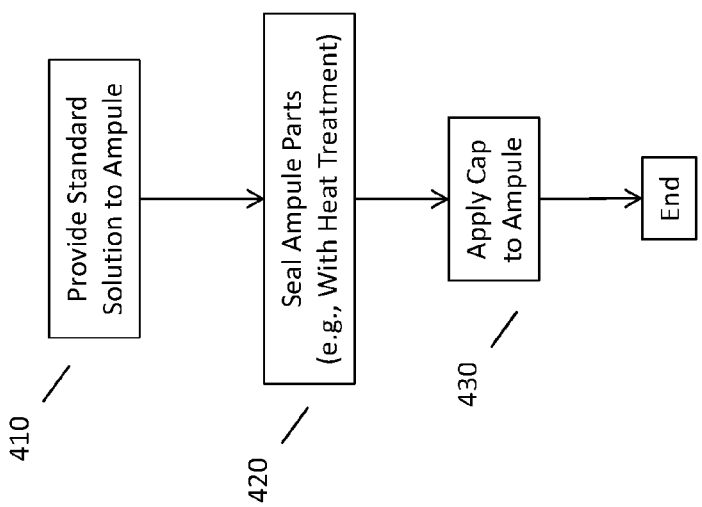
FIG. 4 illustrates an example method of producing an ampule or vial for a turbidity standard according to an embodiment.

As shown in FIG. 4, a method of forming an ampule according to an embodiment includes providing a standard (e.g., formazin standard such as Hach StablCal® standard) at 410 to an ampule, e.g., placing a diluted stabilized formazin standard into the lower or main part of the ampule. Further, the ampule upper and lower parts are sealed, e.g., fused together using heat treatment after the upper part is inserted into the cavity of the lower or main part, as shown at 420. Thereafter, the cap may be applied to the ampule at 430.

Figure 5:
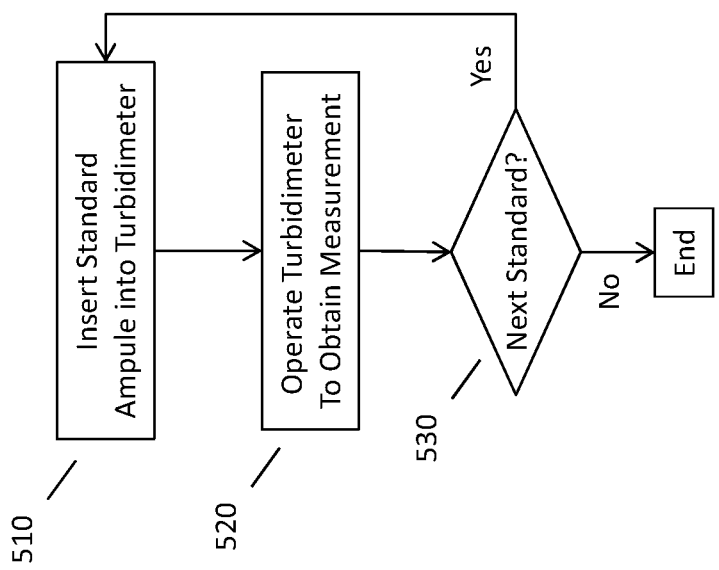
FIG. 5 illustrates an example of using an ampule or vial of standard in a turbidimeter according to an embodiment.
Figure 6:
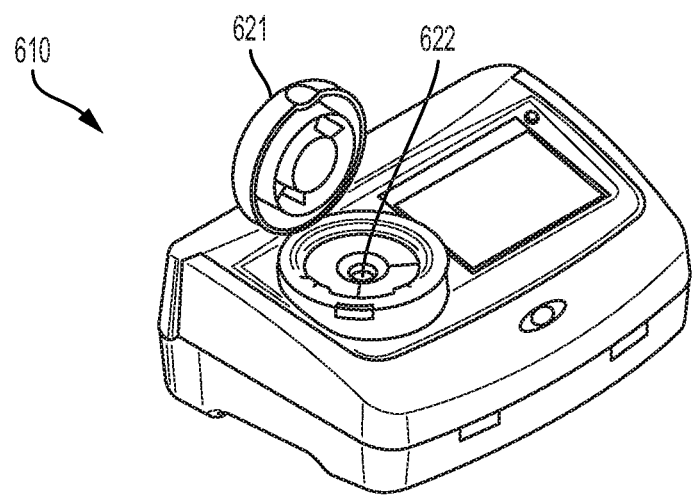
FIG. 6 illustrates an example turbidimeter for using an ampule or vial of standard according to an embodiment.
Figure 7:
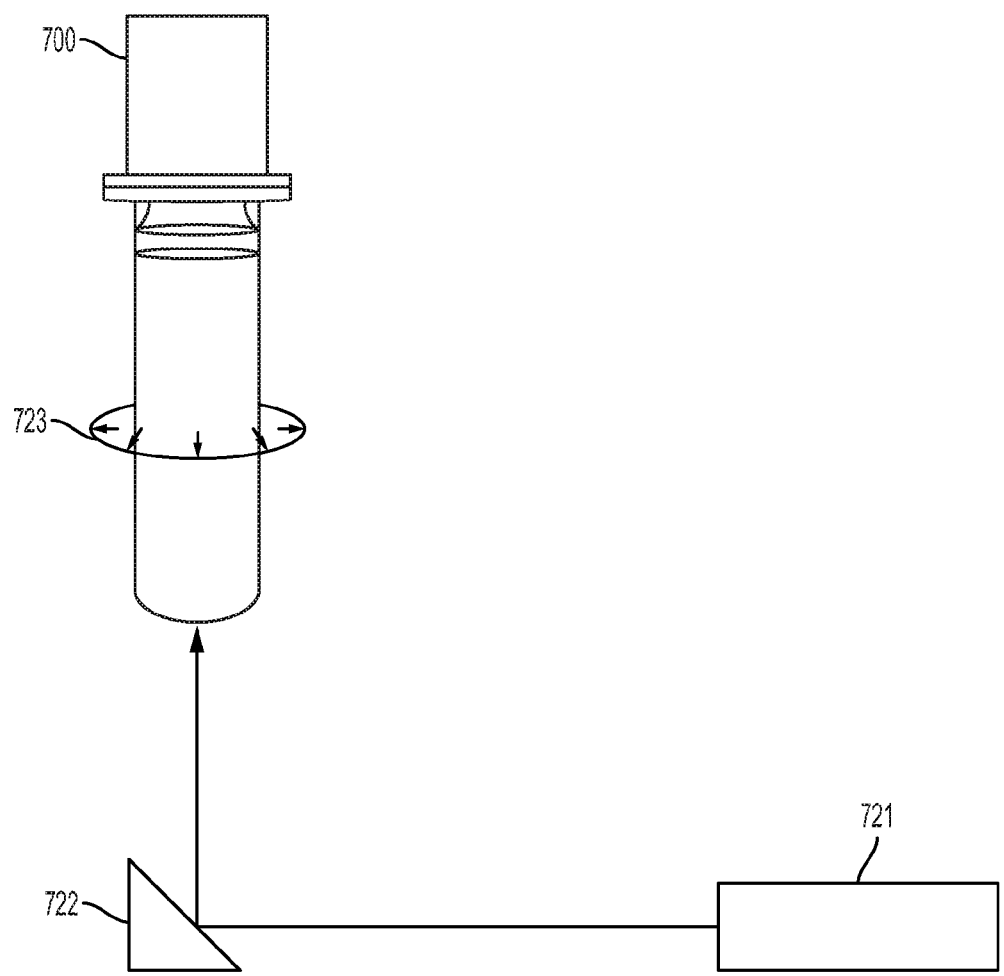
FIG. 7 illustrates an example of light transit through an ampule or vial of standard according to an embodiment.

In order to use the ampule as a standard for a turbidimeter, reference is made to FIG. 5-7. At 510, the ampule is inserted into the turbidimeter. For example, the ampule is inserted at 510 into a turbidimeter. Referring to FIG. 6, specifically the ampule is inserted within a sample compartment 622 of the turbidimeter 610. The lid 621 of the sample compartment 622 is thereafter closed. As may be appreciated, the cap 205/305 of the ampule is made of material blocking light from entering or escaping from the top of the ampule.

As shown in FIG. 5, at 520, the turbidimeter is operated to obtain a measurement (for comparison against the known turbidity of the standard solution). For example, the turbidimeter 610 shown in FIG. 6 is operated to measure the turbidity of the sample contained within the ampule.

Referring briefly to FIG. 7, an example of light transit from a turbidimeter light source to and through the ampule is illustrated. For example, in a method of measurement, a light source 721, e.g., a laser, is operated to provide a light beam that is reflected by a reflecting element 722 (e.g., a mirror) up through the bottom of the ampule 700. The light beam entering the ampule 700 from the bottom is scattered by the formazin standard in a known amount, measured as it exits the ampule 700 as indicated by the arrows exiting from the side of the ampule 700 and is detected by a ring of photodetectors 723.

Referring back to FIG. 5, after a standard measurement has been obtained, it is determined if there is a next standard, as illustrated at 530. If so, another ampule (containing a different formazin standard, e.g., higher or lower NTU value) is inserted and the process is repeated. Thus, an embodiment provides a set or kit that comprises ampules of a range of formazin standards, which may be used to calibrate or standardize a turbidimeter 610, such as that shown in FIG. 6. For example, an ampule according to an embodiment may contain a 20 NTU formazin stock solution therein. Another embodiment provides ampules for a 2 or 3 point calibration, e.g., as specified in the TU 5200 Basic User Manual, DOC022.97.80488 (July 2016), incorporated by reference herein. Otherwise, i.e., if there is no other standard measurement to be made, the process of FIG. 5 ends.

This disclosure has been presented for purposes of illustration and description but is not intended to be exhaustive or limiting. Many modifications and variations will be apparent to those of ordinary skill in the art. The embodiments were chosen and described in order to explain principles and practical application, and to enable others of ordinary skill in the art to understand the disclosure for various embodiments with various modifications as are suited to the particular use contemplated.

Although illustrative embodiments have been described herein, it is to be understood that the embodiments are not limited to those precise embodiments, and that various other changes and modifications may be affected therein by one skilled in the art without departing from the scope or spirit of the disclosure.

What is claimed is:

1. A turbidimeter standard ampule, comprising:
a main part comprising glass and containing therein a formazin solution comprising a formazine polymer diluted in a solvent;
the main part comprising a lens positioned in a bottom edge thereof and permitting entry of light from a turbidimeter;
the main part having glass sides and permitting redirected light to exit the glass sides for detection by a photodetector of the turbidimeter;
an upper part comprising glass and being attached to the main part; and
an opaque cap on the upper part, the opaque cap blocking light from entering the upper part of the ampule.

2. The turbidimeter standard ampule of claim 1, wherein the upper part is attached to the main part by heat treatment.

3. The turbidimeter standard ampule of claim 2, wherein the heat treatment fuses the glass of the upper and main parts to one another.

4. The turbidimeter standard ampule of claim 1, wherein the main part includes a lip that extends circumferentially from the main part and is positioned to seat the ampule within a vial compartment of the turbidimeter.

5. The turbidimeter standard ampule of claim 4, wherein a distance between the lip and a bottom of the main part is about 65 mm.

6. The turbidimeter standard ampule of claim 5, wherein the overall length of the turbidimeter standard ampule is about 108 mm.

7. The turbidimeter standard ampule of claim 1, wherein the main part and the upper part each comprise glass.

8. The turbidimeter standard ampule of claim 1, wherein the ampule does not include plastic in contact with the formazin solution.

9. The turbidimeter standard ampule of claim 1, wherein the upper part is inserted into an opening of the main part prior to attachment of the upper and main parts.

10. The turbidimeter standard ampule of claim 1, wherein the opaque cap is reversibly attached to the upper part.

11. A kit, comprising:
a plurality of turbidimeter standard ampules, each of the plurality of turbidity standard ampules comprising:
a main part comprising glass and containing therein a formazin solution comprise a formazine polymer diluted in a solvent;
the main part comprising a lens positioned in a bottom edge thereof and permitting entry of light from a turbidimeter;
the main part having glass sides and permitting redirected light to exit the glass sides for detection by a photodetector of the turbidimeter;
an upper part comprising glass and being attached to the main part; and
an opaque cap on the upper part, the opaque cap blocking light from entering the upper part of the ampule;
wherein the plurality of turbidity standard ampules comprise a range of different formazin standard solutions.

12. The kit of claim 11, wherein the upper part is attached to the main part by heat treatment.

13. The kit of claim 12, wherein the heat treatment fuses the glass of the upper and main parts to one another.

14. The kit of claim 11, wherein the main part includes a lip that extends circumferentially from the main part and is positioned to seat the ampule within a vial compartment of the turbidimeter.

15. The kit of claim 11, wherein the main part and the upper part each comprise glass.

16. The kit of claim 11, wherein the ampule does not include plastic in contact with the formazin solution.

17. The kit of claim 11, wherein the opaque cap is reversibly attached to the upper part.

* * * * *